(12) United States Patent
Heesch

(10) Patent No.: US 8,627,817 B2
(45) Date of Patent: Jan. 14, 2014

(54) ANESTHESIA DEVICE AND PROCESS FOR OPERATING AN ANESTHESIA DEVICE

(75) Inventor: Ralf Heesch, Lübeck (DE)

(73) Assignee: Dräger Medical GmbH, Lübeck (DE)

( * ) Notice: Subject to any disclaimer, the term of this patent is extended or adjusted under 35 U.S.C. 154(b) by 380 days.

(21) Appl. No.: 12/845,926

(22) Filed: Jul. 29, 2010

(65) Prior Publication Data

US 2011/0061650 A1    Mar. 17, 2011

(30) Foreign Application Priority Data

Sep. 16, 2009  (EP) ..................... 09170436

(51) Int. Cl.
*A61M 16/01* (2006.01)

(52) U.S. Cl.
USPC .................................... 128/203.12

(58) Field of Classification Search
USPC ............ 128/204.18, 204.21, 204.23, 203.12, 128/203.14, 205.24, 200.24, 203.15, 128/205.27–29, 910
See application file for complete search history.

(56) References Cited

U.S. PATENT DOCUMENTS 4,051,847 A * 10/1977 Henkin ..................... 128/202.22
5,520,172 A * 5/1996 Obermayer ............. 128/205.13
6,131,571 A * 10/2000 Lampotang et al. ...... 128/204.21
2004/0168690 A1 * 9/2004 Payne ...................... 128/207.14
2006/0174889 A1   8/2006 Noble

FOREIGN PATENT DOCUMENTS

DE          94 07 417 U1    8/1994
WO      WO 2008/000299     1/2008

* cited by examiner

Primary Examiner — Jackie Ho
Assistant Examiner — Mark Wardas
(74) Attorney, Agent, or Firm — McGlew and Tuttle, P.C.

(57) ABSTRACT

An anesthesia device and a process are provided with which a breathing gas, which is present in a breathing circuit and which is especially enriched with an anesthetic, can be removed rapidly and in a cost-effective manner. The breathing circuit comprises an inspiratory breathing gas duct and an expiratory breathing gas duct, for receiving an expired breathing gas, a Y-piece, which is designed as a Y-piece that can be closed, for connecting the inspiratory and expiratory breathing gas ducts with a patient. At least one breathing gas supply system introduces breathing gas into the breathing circuit. A breathing gas outlet duct is provided with a breathing gas outlet valve. A breathing gas reservoir intermediately stores breathing gas. A PEEP valve is arranged upstream of the breathing gas reservoir in the direction of flow of the breathing gas. A breathing gas delivery is arranged downstream of the breathing gas reservoir in the direction of flow of the breathing gas. An air inlet introduces ambient air into the breathing circuit. The air inlet is arranged between the PEEP valve and the breathing gas delivery. A control is provided at least for controlling the ambient air entering through the air inlet, the breathing gas delivery, the PEEP valve and the breathing gas outlet valve for removing breathing gases from the breathing circuit.

20 Claims, 4 Drawing Sheets

ANESTHESIA DEVICE AND PROCESS FOR OPERATING AN ANESTHESIA DEVICE

CROSS REFERENCE TO RELATED APPLICATIONS

This application claims the benefit of priority under 35 U.S.C. §119 of European Patent Application EP 09 170 436.1 filed Sep. 16, 2009, the entire contents of which are incorporated herein by reference.

FIELD OF THE INVENTION

The present invention pertains to an anesthesia device, with which a breathing gas, which is contained in a breathing circuit and which is especially enriched with an anesthetic, can be rinsed out rapidly and in a cost-effective manner. The present invention is preferably suitable for rinsing out and drying the breathing circuit of the anesthesia device in order to process the breathing circuit with an appropriate control means between two patient treatments automatically or manually by an anesthesiologist or other medical staff. The present invention pertains, in particular, to a so-called rebreathing system, in which $CO_2$ is removed from the expired breathing gas by means of a $CO_2$ absorber and the remaining breathing gas can again be added to the inspiratory breathing gas.

BACKGROUND OF THE INVENTION

A breathing circuit is typically operated in one of two modes of operation: a half-closed mode of operation or as an extensively closed circuit. In the half-closed mode of operation the quantity of breathing gas exceeds the quantity that is taken up by a patient. The excess breathing gas is released from the breathing circuit into an anesthetic removal system during the phase of expiration by the patient. In the mode of operation with the closed breathing circuit, the breathing gases are essentially reprocessed by the $CO_2$ absorber. A suitable absorbent, for example, soda lime, is used for this. The breathing circuit typically comprises an inspiratory breathing gas duct and an expiratory breathing gas duct for making available breathing gas for the patient. The breathing gas is enriched here with anesthetic by means of an anesthetic dispensing means. The inspiratory breathing gas duct and the expiratory breathing gas duct are connected to one another via a so-called Y-piece, which is used via a connected flexible tube to pass on breathing gas to the patient. Up to 5 L of breathing gas are contained in a breathing circuit. Breathing gas of the previous patient may still be present in the breathing circuit between two patient treatments. The breathing circuits of the anesthesia devices can be rinsed out pneumatically, as a rule, only poorly. In particular, intolerance of the breathing gas already used may develop in the next patient. A complicated processing of the breathing circuit by means of a connected simulation lung with simultaneous feed of breathing gas from the breathing gas supply system is, as a rule, necessary for this. To ensure that no anesthetic is present in the components of the breathing circuit, the breathing circuit of the anesthesia device must therefore be rinsed completely. In particular, this measure is significant for the case in which another anesthetic is to be used for the next patient.

Both an anesthesia device and a process for operating the anesthesia device, with which a gas flow of a rinsing gas from a breathing gas supply system is controlled by means of a control means, are disclosed in WO 2008/000 299 A1. Rinsing of the anesthetic from the anesthesia device may now take place when the anesthesia device is not connected to a patient. Gas from the central gas supply system of a hospital is typically used for this. The use of this technical breathing gas for reprocessing the breathing circuit is very cost-intensive.

SUMMARY OF THE INVENTION

The object of the present invention is therefore to make available an anesthesia device for respirating patients, by means of which the above-mentioned drawbacks are overcome. A special object of the present invention is to make available a process for operating the anesthesia device, by means of which a simple processing of the anesthesia device between the individual patients can be carried out.

According to the invention, an anesthesia device is provided with a breathing circuit comprising an inspiratory breathing gas duct and an expiratory breathing gas duct for receiving an expired breathing gas. A Y-piece designed as a closable Y-piece connects the inspiratory and expiratory breathing gas ducts with a patient. At least one breathing gas supply system is provided for introducing breathing gas into the breathing circuit. A breathing gas outlet duct is provided with a breathing gas outlet valve. A breathing gas reservoir intermediately stores breathing gas. A Positive End Expiratory Pressure (PEEP) valve is arranged upstream of the breathing gas reservoir in the direction of flow of the breathing gas. A breathing gas delivery means is arranged downstream of the breathing gas reservoir in the direction of flow of the breathing gas. An air inlet introduces ambient air into the breathing circuit. The air inlet is arranged between the PEEP valve and the breathing gas delivery means. A control means is provided at least for controlling the ambient air entering through the air inlet, breathing gas delivery means, the PEEP valve and breathing gas outlet valve for removing breathing gases from the breathing circuit.

According to another aspect of the invention, a process is provided for operating the anesthesia device of the invention. The process includes the following process steps:
  A: Closure of the Y-piece,
  B: Closure of the PEEP valve,
  C: Opening of the breathing gas outlet valve,
  D: Opening of the air inlet, and
  E: Start of the breathing gas delivery device,
so that ambient air is drawn in by the breathing gas delivery means and a breathing gas is thus delivered from the breathing circuit.

An essential advantage of the anesthesia device according to the present invention is that no cost-intensive technical breathing gases, which are made available by the central gas supply system, are necessary for processing between the individual patient treatments. The breathing gas can be advantageously delivered from the breathing circuit by means of the ambient air, which is drawn in through an air inlet in the breathing circuit by the breathing gas delivery means. The breathing circuit of the anesthesia device according to the present invention comprises in this case an inspiratory breathing gas duct and an expiratory breathing gas duct, a Y-piece, which is designed as a closable Y-piece, for connecting the inspiratory and expiratory breathing gas ducts to the patient access. The Y-piece is typically closed by means of a sealing plug (or sealing cone). Furthermore, a central gas supply system for introducing breathing gas into the breathing circuit, a breathing gas delivery means, a breathing gas outlet duct with a breathing gas outlet valve, a breathing gas reservoir for intermediately storing breathing gas, a PEEP valve arranged upstream of the breathing gas reservoir in the direction of flow of the breathing gas, a breathing gas delivery means arranged downstream of the breathing gas reservoir in the direction of flow of the waste gas, an air inlet for introducing ambient air into the breathing circuit and a control means are provided. The air inlet is arranged between the PEEP valve and the breathing gas delivery means. The control means is used at least to control the ambient air entering through the air inlet, breathing gas delivery means, PEEP valve and breathing gas outlet valve for removing breathing gases from the breathing circuit. In a preferred embodiment, the air inlet is arranged such that it is arranged downstream of the breathing gas reservoir in the breathing circuit. A vacuum, which brings about a flow of the breathing gas present in the breathing gas reservoir through the breathing gas circuit to a breathing gas outlet duct, can thus be advantageously generated according to the process steps according to the present invention after closing the Y-piece and the PEEP valve, opening of the breathing gas outlet valve and the air inlet and after starting the breathing gas delivery means.

At least a first part of the inner breathing circuit of the anesthesia device can thus be advantageously freed from breathing gas by means of ambient air. In another advantageous embodiment of the anesthesia device according to the present invention, a first volume flow sensor is provided in the breathing circuit, preferably in the expiratory breathing gas duct. The first volume flow sensor measures the volume flow after the start of the breathing gas delivery means. After reaching a predetermined breathing gas volume, the breathing gas outlet valve is closed and the PEEP valve is opened. The residual part of the inner breathing circuit of the anesthesia device is thus also freed from breathing gas in a second phase.

Switchover from the first phase of the process according to the present invention to a second phase, according to another advantageous embodiment of the process according to the present invention, takes place at a volume flow value that corresponds essentially to the volume of the part of the breathing circuit that is to be cleaned in the first phase. The volume is in the range of preferably 10 L to 15 L. The breathing gas delivery means advantageously operates at a rate of preferably 50 L to 100 L per minute.

As an alternative to the measurement of the volume flow, a time can be measured as a criterion for switching over from the first to the second phase. The time preferably equals 15-45 seconds.

In another embodiment of the anesthesia device according to the present invention, a second volume flow sensor is provided in the breathing circuit, preferably in the inspiratory breathing gas duct. Proper closing of the Y-piece according to process step A can be checked by forming the difference of the volume flow values of the first and second volume flow sensors and an alarm is generated.

A concentration of anesthetic still present in the breathing circuit can be checked, furthermore, by means of a gas measuring module arranged preferably between the Y-piece and the air inlet. Corresponding to the concentration of anesthetic still present, process steps A through E of the process according to the present invention can be repeated as often as desired. As an alternative to this, a duration for carrying out the process according to the present invention can be selected by the user.

The anesthesia device according to the present invention may provide, furthermore, a $CO_2$ absorber in the breathing circuit, which is preferably arranged downstream of the breathing gas reservoir. The breathing gas expired by the patient is separated from $CO_2$ by means of a $CO_2$ absorber. Moisture and heat are produced, among other things, during this separation. Together with the moisture expired by the patient, condensation may frequently occur within the breathing circuit. The functionality of the breathing circuit may be compromised because of the accumulation of this condensate over a plurality of consecutive applications. To remove this moisture, a drying effect of the breathing circuit is achieved in a next step of the process according to the present invention by repeating the process steps several times. This so-called drying phase ensures that the lime will not dry out completely within the $CO_2$ absorber because of the ambient air used. In addition, a heater, which is advantageously operated at a higher heating output than in the normal patient respiration mode, may be provided within the breathing circuit. This advantageously leads to acceleration of drying.

The present invention will be described now on the basis of an example with reference to the drawings. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
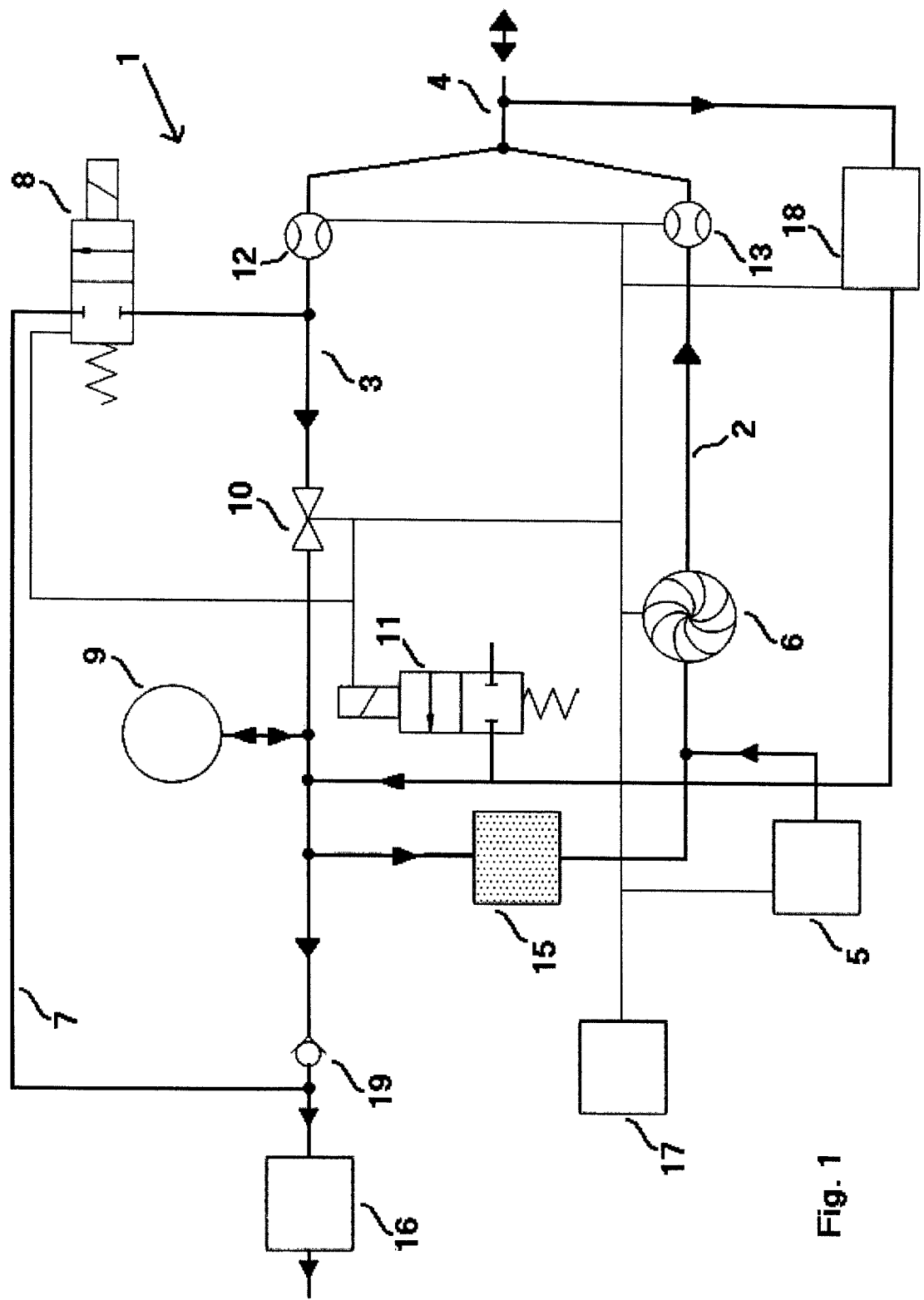
FIG. 1 is a schematic view of a breathing circuit of the anesthesia system according to the present invention.

Referring to the drawings in particular, FIG. 1 shows a schematic view of the anesthesia device according to the present invention with a breathing circuit 1. Breathing circuit 1 is designed in the form of a rebreathing system, in which $CO_2$ is removed from a breathing gas expired by the patient by a $CO_2$ absorber. This breathing gas is subsequently added again to the inspiratory breathing gas. Only the breathing gas consumed by the patient is replaced in such a rebreathing system. The rest is reused from the expiratory breathing gas. The respective breathing gas pathways are indicated by bold lines in FIG. 1, whereas the thin lines represent control and data lines between the individual components of breathing circuit 1.

Breathing gas is fed to the breathing circuit 1 from a breathing gas supply system 5. The breathing gas is usually processed in the corresponding medical means and comprises essentially an oxygen-air mixture, $N_2O$ and volatile gaseous anesthetics. A breathing gas delivery means 6 delivers this breathing gas via an inspiratory breathing gas duct 2 to a Y-piece 4. Furthermore, an inspiratory nonreturn valve (not shown) is present in the inspiratory breathing gas duct 2. The patient to be respirated is connected to the Y-piece 4 via a tube (not shown). The breathing gas expired by the patient is in turn sent during the phase of expiration via the Y-piece 4 and an expiratory breathing gas duct 3 via a PEEP valve 10. An expiratory nonreturn valve (not shown) is arranged in the expiratory breathing gas duct 3. Furthermore, the expired breathing gas is stored intermediately in a breathing gas reservoir 9 in the breathing circuit 1. A $CO_2$ absorber 15 is arranged downstream of the breathing gas reservoir 9. $CO_2$ is removed from the breathing gas in the $CO_2$ absorber and the breathing gas thus purified is subsequently fed again into the inspiratory breathing gas duct 2.

If the breathing gas reservoir 9 is filled sufficiently, excess breathing gas can be released into an anesthetic removal system 16 connected to the breathing circuit 1.

The breathing gas pressures present can be monitored by means of pressure sensors (not shown) in both the inspiratory breathing gas duct 2 and the expiratory breathing gas duct 3. An expiratory volume flow of the breathing gas is measured by means of a first volume flow sensor 12. Volume flow sensor 12 is arranged in the expiratory breathing gas duct 3. A second volume flow sensor 13 is located in the inspiratory breathing gas duct 2 and measures the volume flow of the inspiratory breathing gas. The breathing gas delivery means 6 stops the breathing gas volume delivery during an expiration phase of the patient (expiration phase) and the PEEP valve 10 is set to a final value of a desired expiratory pressure. The volume being stored intermediately in the patient can again flow back into breathing circuit 1. The breathing gas volume thus released is measured and monitored by means of the first volume flow sensor 12. A concentration of the breathing gas is monitored by means of a breathing gas measuring device 18 during respiration of a patient.

Breathing circuit 1 of the anesthesia device according to the present invention contains, furthermore, an air inlet 11 for introducing ambient air into the breathing circuit 1. The air inlet 11 is closed during normal respiration of a patient. The breathing gas outlet duct 7 is likewise separated from the breathing circuit 1 by a closed breathing gas outlet valve 8. In case the breathing gas pressure is too high, the breathing gas outlet valve 8 can be opened in order to release the excessively high breathing gas pressure into the anesthetic removal system 16 via the breathing gas outlet duct 7. Both automatic patient respiration and manual respiration of a patient may take place with the anesthesia device according to the present invention shown.

Figure 2:
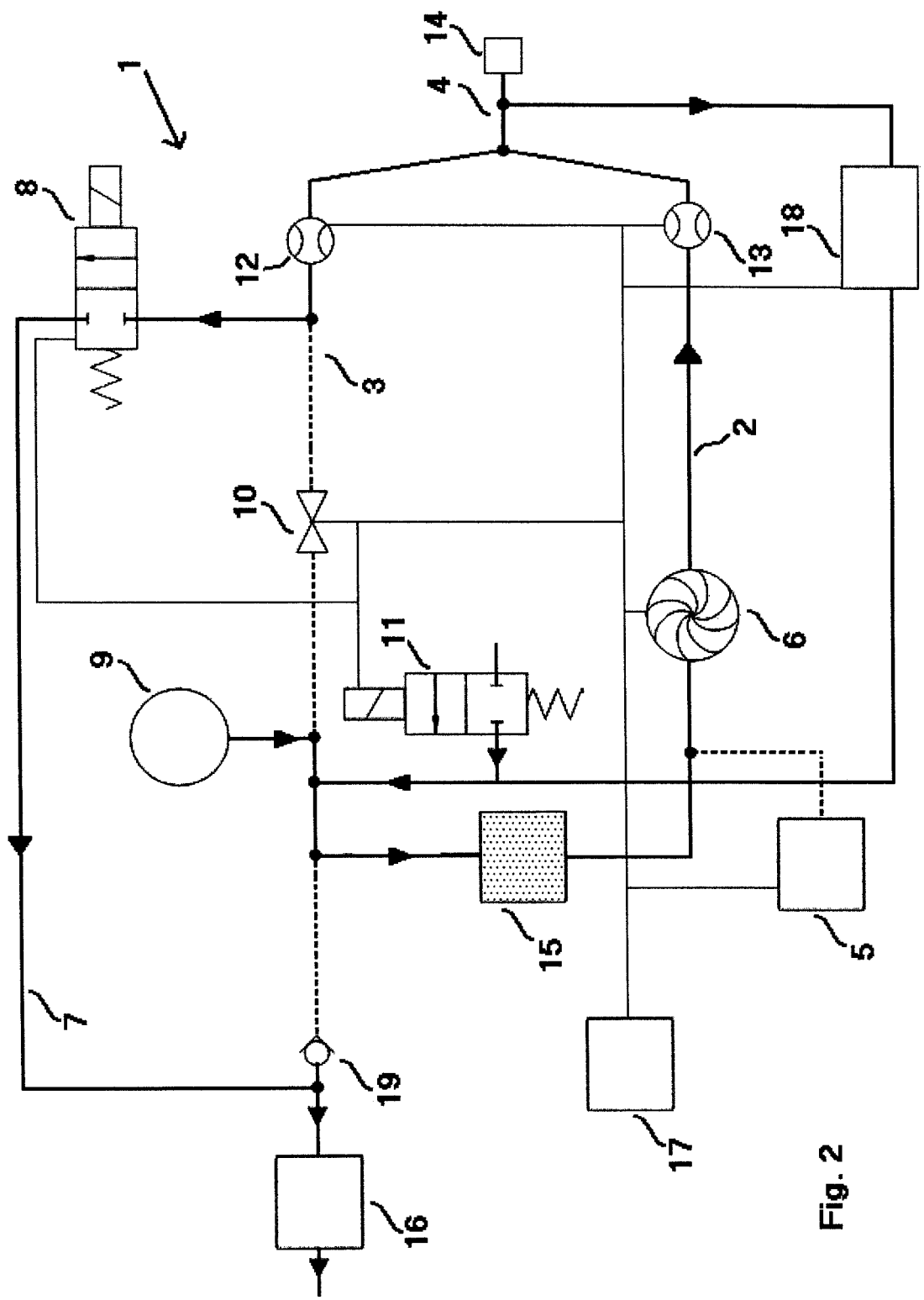
FIG. 2 is a schematic view of the anesthesia system according to the present invention during the performance of the process according to the present invention in a first embodiment.

FIG. 2 schematically shows the principle of the process according to the present invention. The Y-piece is closed in a first process step. A sealing cone 14 is located for this at the anesthesia apparatus. The patient-side port of the Y-piece 4 is attached to the sealing cone 14. As an alternative, an automatic closing device may be provided as well.

The PEEP valve 10 is closed in a subsequent process step, so that a connection between the Y-piece 4 and the breathing gas reservoir 9 is interrupted via the expiratory breathing gas duct 3. The blocked areas of the breathing gas ducts in breathing circuit 1 are marked by broken lines. The breathing gas outlet valve 8 is opened, so that there is a connection between the Y-piece 4 and the breathing gas outlet duct 7 to the anesthetic removal system 16. The air inlet 11 is subsequently opened and the breathing gas delivery means 6 is simultaneously or subsequently activated. Ambient air is thus drawn in by the breathing gas delivery means 6. As a result, a vacuum is generated on the suction side of the breathing gas delivery means 6. The vacuum causes the total breathing gas volume to be delivered at first out of the breathing gas reservoir 9 and delivered via the breathing gas outlet duct 7 into the anesthetic removal system 16. The essential components of the breathing circuit 1 are thus already freed from breathing gas. The air inlet has a nominal diameter of preferably 5 mm to 6 mm. A sufficient vacuum can be generated for the breathing gas reservoir 9 with these dimensions. At the same time, a sufficient volume flow can thus be guaranteed. The anesthetic removal system 16 has a maximum capacity of 25 L to 50 L per minute for breathing gas enriched with anesthetic. The breathing gas delivery means 6 operates with these parameters with a volume delivery flow of 25 L to 50 L per minute.

The process according to the present invention forms a first essential phase for removing breathing gas from the breathing circuit 1 shown, preferably between the treatment of two patients.

Figure 3:
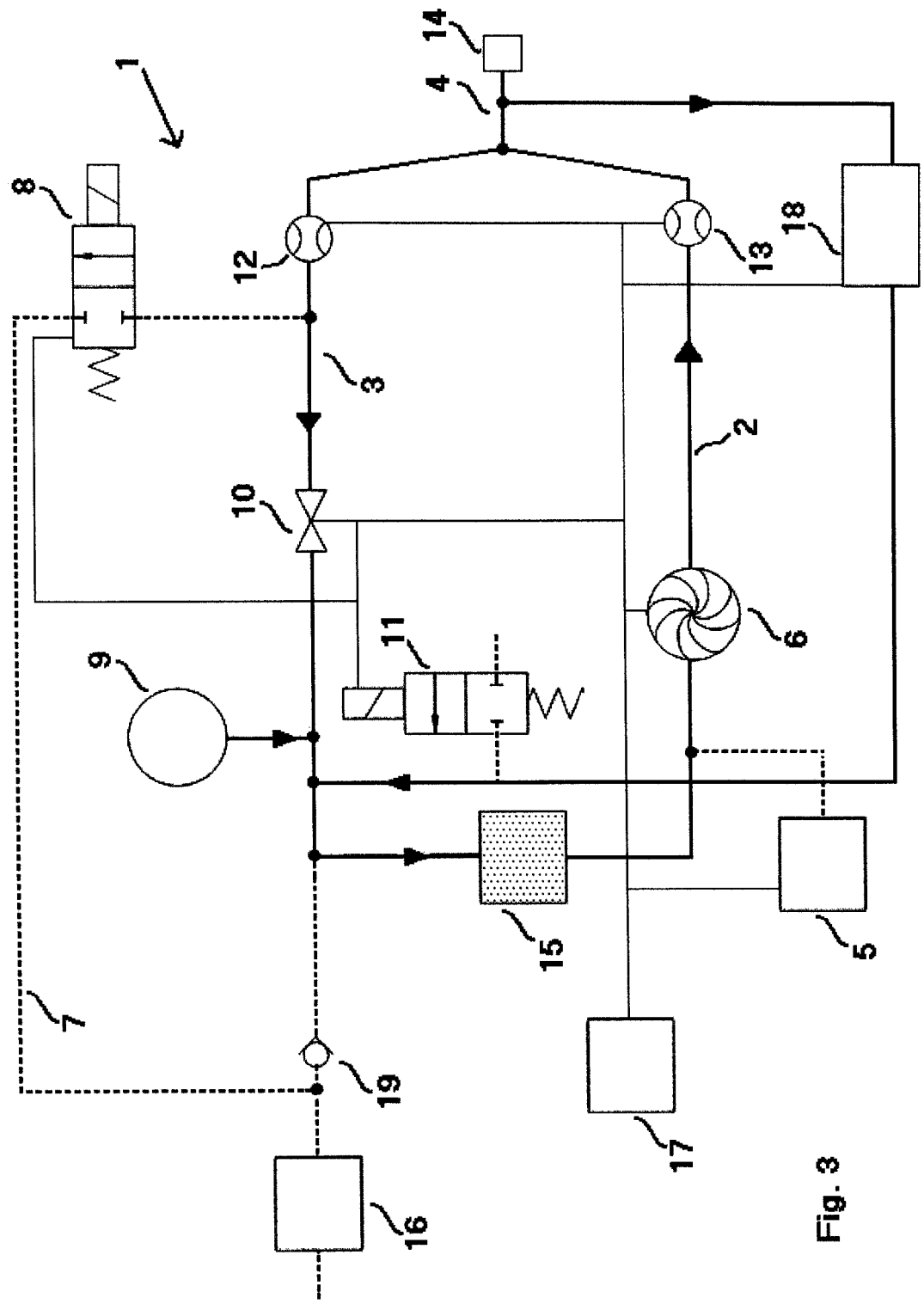
FIG. 3 is a schematic view of the anesthesia system according to the present invention during the performance of the process according to the present invention in a second embodiment.

To also remove breathing gas from the area between the PEEP valve 10 and the breathing gas reservoir 9 of breathing circuit 1, the breathing gas outlet valve 8 is closed and the PEEP valve 10 is opened in another embodiment of the process according to the present invention. This state represents a second phase of the processing of the breathing circuit, shown in FIG. 3. A predefined breathing gas volume or a time may be used as a switchover point between the first and second phases. A measurement of the breathing gas volume is preferably carried out with the first volume flow sensor 12 in the expiratory breathing gas duct. The beginning of the measurement of both a breathing gas volume and a time is after the start of the breathing gas delivery means 6. A predetermined value of the breathing gas volume is advantageously 1 L to 2 L. This value typically corresponds to 2 to 3 times the volume of breathing gas of the part of the breathing circuit 1 from which breathing gas is to be removed. The time needed for this in case of a breathing gas volume, driven by the breathing gas delivery means 6, of 50 L to 100 L per minute, is approximately 1 second The process according to the present invention is preferably carried out in phase 1 once again after this.

A breathing gas measuring device 18 arranged between the breathing gas reservoir 9 and the Y-piece 4 can determine the concentration of breathing gas still present, so that the cycles of the process according to the present invention are preferably run through in phase 1 and, in the further embodiment of the process according to the present invention in phase 2, until a desired breathing gas concentration is reached.

The breathing gas measuring device 18 draws off part of the volume flow during the processing of breathing circuit 1 in order to thus also remove breathing gas from this breathing gas pathway. At the same time, the breathing gas measuring device 18 can monitor the rinsing operation or the efficacy thereof in respect to a lowering of a breathing gas concentration. The number of sequences of the process according to the present invention, which are to be run through, can thus be determined with the breathing gas measuring device 18. As an alternative to this, the user can select the duration or the number of runs of the process according to the present invention.

For drying the breathing circuit 1, an exchange of the moist breathing gas present in the breathing circuit with external, dry ambient air is achieved. Several cycles of the process according to the present invention and optionally of the further embodiment of the process according to the present invention in a phase 2 are necessary for drying out the breathing circuit 1. A drying operation of the breathing circuit 1 can be advantageously carried out at the end of the use of the anesthesia device. This may happen, for example, by a therapist or anesthesiologist starting the drying operation at the anesthesia device. The anesthesia device may be designed to shut off after a predefined or settable time.

Acceleration of the drying operation can be achieved by heating the components of the breathing circuit 1. A heating device can set a higher heating temperature compared to a normal mode of respiration of a patient. An advantage of the drying operation with ambient air compared to the technical gases used according to the state of the art is that a certain residual humidity is contained in the ambient air. This is seemingly disadvantageous in the sense of rapid drying, but it ensures that lime within the $CO_2$ absorber 15 cannot dry out completely. Completely dried lime of the $CO_2$ absorber 15 has a relatively short service life in the sense of $CO_2$ absorption. Furthermore, it has the property of splitting volatile gaseous anesthetics (especially isoflurances) and producing toxic substances in the process. Thus, the use of ambient air for drying the breathing circuit 1 of the anesthesia device according to the present invention with ambient air represents an important function in respect to patient safety.

In another embodiment of the process according to the present invention, a Y-piece that is not closed correctly can be recognized and an alarm can be triggered by forming the difference of the first volume flow sensor 12 and the second volume flow sensor 13. This is carried out by means of inspiratory volume flow measurement, measured with the second inspiratory volume flow sensor 13 minus the expiratory volume flow measured by means of the expiratory volume flow measurement. If this volume flow difference becomes greater, for example, 20% of the inspiratory volume flow, leakage in the breathing circuit 1 or an incorrectly closed Y-piece 4 can be inferred. This can be advantageously displayed for the user at the anesthesia device. As an alternative to this, the user can select the duration or the number of runs of the process according to the present invention.

A further optimization of the time needed for the process according to the present invention can be adapted to the particular specific volumes of the respective breathing circuits 1. The volume of the corresponding breathing gas ducts can be determined by a compliance measurement. The compliance measurement can be carried out within the framework of a switch-on test. The anesthesia device according to the present invention can thus be adapted to the particular prevailing variable patient conditions. A time needed for carrying out the drying of the breathing circuit 1 can be based on empirically determined data or on a moisture measurement integrated in breathing circuit 1. If the duration of the drying function is determined on an empirical basis, the duration should be increased with the duration of use of the breathing circuit 1 since the drying function carried out last. The longer the time during which a relatively small breathing gas flow was made available by the breathing gas supply system 5 during this use time, the longer should be the duration selected for the drying function.

Figure 4:
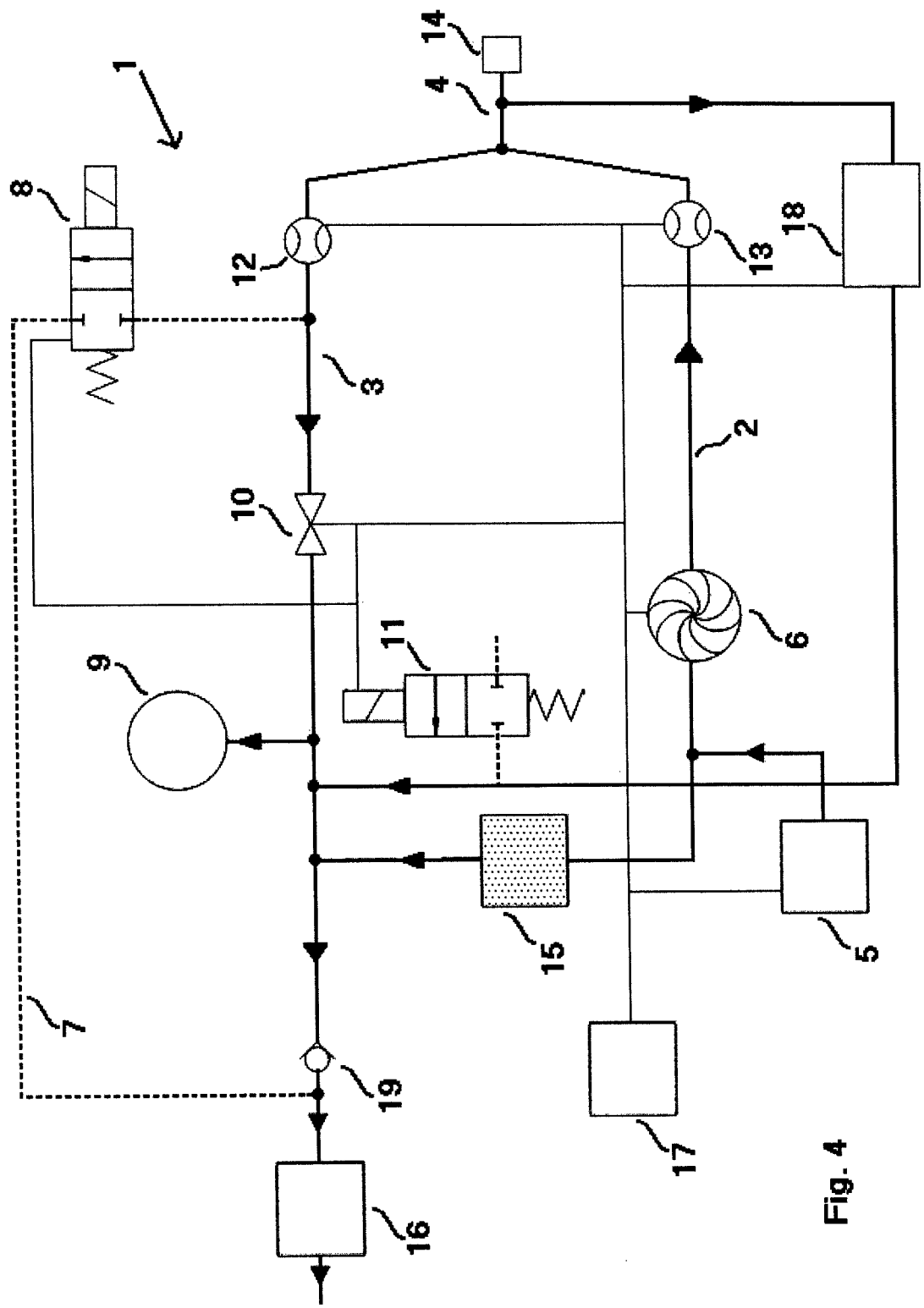
FIG. 4 is a schematic view of the anesthesia system according to the present invention in another embodiment of the process according to the present invention (drying function).

Dry gas can be fed from the central gas supply system into the breathing circuit 1 for a further optimization of the drying of the breathing circuit 1. The breathing gas delivery means 6 is set here such that about half of the dry gas is passed through the inspiratory breathing gas duct 2. The other half is sent through the $CO_2$ absorber contrary to the usual direction of the breathing gas. Both the first and second halves of gas are sent into the anesthetic removal system 16 via the nonreturn valve 19 (FIG. 4). The temperature drops in breathing circuit 1 especially after switching off the heater, which causes increased condensation. This condensation is advantageously avoided by the dry gas introduced.

The process according to the present invention can take place within the framework of a switch-off procedure. This occurs according to the present invention, between the use of the anesthesia device on two patients and during a switch-off procedure.

While specific embodiments of the invention have been described in detail to illustrate the application of the principles of the invention, it will be understood that the invention may be embodied otherwise without departing from such principles.

LIST OF REFERENCE NUMBERS

1. Breathing circuit
2. Inspiratory breathing gas duct
3. Expiratory breathing gas duct
4. Y-piece
5. Breathing gas supply system
6. Breathing gas delivery means
7. Breathing gas outlet duct
8. Breathing gas outlet valve
9. Breathing gas reservoir
10. PEEP valve
11. Air inlet
12. First volume flow sensor
13. Second volume flow sensor
14. Sealing cone
15. $CO_2$ absorber
16. Anesthetic removal system
17. Control device
18. Breathing gas measuring device
19. Nonreturn valve

What is claimed is:

1. An anesthesia device comprising:
a breathing circuit including an inspiratory breathing gas duct and an expiratory breathing gas duct receiving an expired breathing gas;
a closable patient connection for connecting to the inspiratory breathing gas duct and expiratory breathing gas duct, the closable patient connection including a sealing cone for closing a patient connection patient end to provide a closed patient connection state in which the inspiratory breathing gas duct and the expiratory breathing gas duct of the breathing circuit remain connected and the breathing circuit is disconnected from the patient connection patient end or an automatic closing device to provide the closed patient connection state;
a breathing gas supply system introducing breathing gas into the breathing circuit;
a breathing gas outlet duct with a breathing gas outlet valve having a closed state and an open state, the breathing gas outlet duct being connected to the expiratory breathing gas duct and removing gas from the breathing circuit with the breathing gas outlet valve in the open state;
a breathing gas reservoir for intermediately storing breathing gas,
a PEEP valve arranged in the breathing circuit upstream of the breathing gas reservoir in a direction of flow of the breathing gas and downstream of the breathing gas outlet duct in the direction of flow of the breathing gas;
a breathing gas delivery means arranged in the breathing circuit downstream of the breathing gas reservoir in the direction of flow of the breathing gas;
an air inlet for introducing ambient air into the breathing circuit, wherein the air inlet is arranged between the PEEP valve and the breathing gas delivery means; and
a control means for controlling the ambient air entering through the air inlet, for controlling the breathing gas delivery means, for controlling the PEEP valve with the patient connection in the closed patient connection state and for controlling the breathing gas outlet valve, the control means, during a first phase, closing the PEEP valve, with the patient connection in the closed patient connection state, opening the breathing gas outlet valve and opening the air inlet and establishing a first phase gas flow path from the air inlet, through the breathing gas delivery means and through the breathing gas outlet duct, the first phase gas flow path being in flow connection with the breathing gas reservoir to cause a breathing gas volume to be delivered out of the breathing gas reservoir via the breathing gas outlet duct, based on the operation of the gas delivery means, for removing breathing gases from the breathing circuit and the control means, during a second phase, opening the PEEP valve, with the patient connection in the closed patient connection state, closing the breathing gas outlet valve and closing the air inlet and establishing a second phase gas flow path providing a circulation of gas in the breathing circuit to move breathing gas from an area between the PEEP valve and the breathing gas reservoir.

2. An anesthesia device in accordance with claim 1, wherein a sealing cone is provided for closing the patient connection.

3. An anesthesia device in accordance with claim 1, wherein the air inlet is arranged downstream of the breathing gas reservoir in the breathing circuit.

4. An anesthesia device in accordance with claim 1, further comprising a first volume flow sensor provided in the breathing circuit in the expiratory breathing gas duct.

5. An anesthesia device in accordance with claim 4, further comprising a second volume flow sensor in the breathing circuit in the inspiratory breathing gas duct, wherein a proper closing of the patient connection in a closed patient connection state is determined by forming a difference of the values of the first volume flow sensor and the second volume flow sensor.

6. An anesthesia device in accordance with claim 1, further comprising a $CO_2$ absorber provided in the breathing circuit arranged downstream of the breathing gas reservoir.

7. An anesthesia device in accordance with claim 1, further comprising a breathing gas measuring device for monitoring a concentration of anesthetic in the breathing gas, the breathing gas measuring device being arranged between the patient connection and the air inlet.

8. A process for operating an anesthesia device, the process comprising the steps of:
providing a breathing circuit including a closable Y-piece, an inspiratory breathing gas duct and an expiratory breathing gas duct, the closable Y-piece connecting the inspiratory breathing gas duct and expiratory breathing gas duct with a patient;
providing a breathing gas supply system introducing breathing gas into the breathing circuit;
providing a breathing gas outlet duct with a breathing gas outlet valve having a closed state and an open state, the breathing gas outlet duct being connected to the expiratory breathing gas duct and removing gas from the breathing circuit with the breathing gas outlet valve in the open state;
providing a breathing gas reservoir for intermediately storing breathing gas;
providing a PEEP valve arranged in the breathing circuit upstream of the breathing gas reservoir in a direction of flow of the breathing gas and downstream of the breathing gas outlet duct in the direction of flow of the breathing gas;
providing a breathing gas delivery means arranged in the breathing circuit downstream of the breathing gas reservoir in the direction of flow of the breathing gas;
providing an air inlet for introducing ambient air into the breathing circuit, wherein the air inlet is arranged between the PEEP valve and the breathing gas delivery means;
providing a control device;
closing the Y-piece with the control device or by applying a sealing cone to provide a closed Y-piece state in which the inspiratory breathing gas duct and the expiratory breathing gas duct of the breathing circuit remain connected and the breathing circuit is disconnected from the Y-piece patient end;
closing the PEEP valve with the control device;
opening the breathing gas outlet valve with the control device;
opening the air inlet with the control device; and
starting the breathing gas delivery means with the control device so that ambient air is drawn in by the breathing gas delivery means and breathing gas is delivered from the breathing circuit and a first phase gas flow path is established from the air inlet, through the breathing gas delivery means and through the breathing gas outlet duct, the first phase gas flow path being in flow connection with the breathing gas reservoir to cause a breathing gas volume to be delivered out of the breathing gas reservoir via the breathing gas outlet duct, based on the operation of the gas delivery means, for removing breathing gases from the breathing circuit.

9. A process for operating an anesthesia device in accordance with claim 8, wherein a breathing gas volume is measured with a first volume flow sensor and/or a time is measured subsequent to starting the breathing gas delivery means.

10. A process for operating an anesthesia device in accordance with claim 9, wherein after reaching a predetermined breathing gas volume and/or a predetermined time, the breathing gas outlet valve is closed and the PEEP valve is opened and a second phase gas flow path is established providing a circulation of gas in the breathing circuit to move breathing gas from an area between the PEEP valve and the breathing gas reservoir.

11. A process for operating an anesthesia device in accordance with claim 10, wherein a breathing gas volume and/or time is measured.

12. A process for operating an anesthesia device in accordance with claim 11, wherein after reaching the predetermined breathing gas volume and/or time, the process steps involving control with the control device for closing the Y-piece, closing the PEEP valve, opening the breathing gas outlet valve, opening of the air inlet and starting the breathing gas delivery device is started again or the Y-piece is opened and the air inlet is closed.

13. A process for operating an anesthesia device in accordance with claim 12, wherein a volume flow corresponds at least to a volume of a portion of the expiratory breathing gas duct between the PEEP valve and a port to the breathing gas reservoir.

14. A process for operating an anesthesia device in accordance with claim 8, wherein dry gas is fed into the breathing circuit from a central gas supply system, wherein the breathing gas delivery means is set such that a portion of the dry gas that is fed is sent through the inspiratory breathing gas duct and a portion of the dry gas that is fed is fed into the breathing circuit in a direction opposite to a direction of the inspiratory breathing gas duct.

15. An anesthesia device comprising:
a breathing circuit including an inspiratory breathing gas duct and an expiratory breathing gas duct receiving an expired breathing gas;

a closable Y-piece for connecting the inspiratory breathing gas duct and the expiratory breathing gas duct with a patient, the closable Y-piece including a sealing cone to provide a closed Y-piece state in which the inspiratory breathing gas duct and the expiratory breathing gas duct of the breathing circuit remain connected and the breathing circuit is disconnected from the Y-piece patient end or an automatic closing device to provide the closed Y-piece state;

a breathing gas supply system introducing breathing gas into the breathing circuit;

a breathing gas outlet duct with a breathing gas outlet valve having a closed state and an open state, the breathing gas outlet duct being connected to the expiratory breathing gas duct and removing gas from the breathing circuit with the breathing gas outlet valve in the open state;

a breathing gas reservoir for intermediately storing breathing gas, a PEEP valve arranged in the expiratory breathing gas duct upstream of the breathing gas reservoir in a direction of flow of the breathing gas and downstream of the breathing gas outlet duct in the direction of flow of the breathing gas;

a breathing gas delivery means arranged in the breathing circuit downstream of the breathing gas reservoir in the direction of flow of the breathing gas;

an air inlet for introducing ambient air into the breathing circuit, wherein the air inlet is arranged between the PEEP valve and the breathing gas delivery means; and a control means for controlling the air inlet such that the ambient air enters through the air inlet, for controlling the breathing gas delivery means, for controlling the PEEP valve to close the PEEP valve with the Y-piece in the closed Y-piece state and for controlling the breathing gas outlet valve to open the breathing gas outlet valve to establish a first phase gas flow path from the air inlet, through the breathing gas delivery means and through the breathing gas outlet duct, the first phase gas flow path being in flow connection with the breathing gas reservoir to cause a breathing gas volume to be delivered out of the breathing gas reservoir via the breathing gas outlet duct, based on the operation of the gas delivery means, for removing breathing gases from the breathing circuit and to establish a second phase flow path from the air inlet, through the breathing gas delivery means and through the PEEP valve, to move breathing gas from an area between the PEEP valve and the breathing gas reservoir.

16. An anesthesia device in accordance with claim 15, wherein the first phase gas flow path is formed by closing the Y-piece so that a connection between the Y-piece and the breathing gas reservoir is interrupted, whereby with the breathing gas outlet valve opened the control means removes breathing gases from the breathing circuit by suctioning air through the open air inlet with the breathing gas delivery means.

17. An anesthesia device in accordance with claim 16, wherein the second phase gas flow path is formed by closing the breathing gas outlet valve with the control means and opening the PEEP valve with the control means.

18. An anesthesia device in accordance with claim 15, further comprising a breathing gas measuring device for monitoring a concentration of anesthetic in the breathing gas, the breathing gas measuring device being arranged between the Y-piece and the air inlet.

19. An anesthesia device in accordance with claim 15, further comprising:
a first volume flow sensor provided in the breathing circuit in the expiratory breathing gas duct; and
a second volume flow sensor in the breathing circuit in the inspiratory breathing gas duct, wherein a proper closing of the Y-piece in the closed Y-piece state is determined by forming a difference of the values of the first volume flow sensor and the second volume flow sensor.

20. An anesthesia device in accordance with claim 15, further comprising a $CO_2$ absorber provided in the breathing circuit arranged downstream of the breathing gas reservoir.

* * * * *